United States Patent [19]
Matthai et al.

[11] Patent Number: 5,702,415
[45] Date of Patent: Dec. 30, 1997

[54] CHUCK AND BLADE FOR POWERED MEDICAL HANDPIECE

[75] Inventors: John T. Matthai; Richard F. Huyser, both of Kalamazoo, Mich.

[73] Assignee: Stryker Corporation, Kalamazoo, Mich.

[21] Appl. No.: 526,054

[22] Filed: Sep. 8, 1995

Related U.S. Application Data

[62] Division of Ser. No. 326,043, Oct. 19, 1994, Pat. No. 5,468,247, which is a continuation of Ser. No. 67,740, May 26, 1993, abandoned.

[51] Int. Cl.⁶ .................................................. A61B 17/14
[52] U.S. Cl. .......................... 606/178; 606/82; 30/339; 83/676; 83/698.41
[58] Field of Search ............................. 606/178, 177, 606/176, 179, 82; 30/392, 393, 329, 337, 339, 277.4; 83/676, 698.41, 698.61

[56] References Cited

U.S. PATENT DOCUMENTS

| | | |
|---|---|---|
| 44,823 | 10/1864 | Rose . |
| D. 198,423 | 6/1964 | Cummins . |
| D. 239,331 | 3/1976 | Treace . |
| D. 245,918 | 9/1977 | Shen ................................. D24/140 |
| D. 282,142 | 1/1986 | Siravo . |
| D. 294,734 | 3/1988 | Detsch ............................... D24/147 |
| D. 316,220 | 4/1991 | Ailey et al. . |
| D. 317,821 | 6/1991 | Aoyagi .............................. D24/136 |
| D. 337,160 | 7/1993 | Evans . |
| D. 343,247 | 1/1994 | Walen . |
| D. 351,907 | 10/1994 | Matthai et al. .................... D24/146 |
| 436,804 | 9/1890 | Roberts . |
| 1,048,085 | 12/1912 | MacFarland . |
| 1,064,493 | 6/1913 | Kropat . |
| 1,125,234 | 1/1915 | White . |
| 1,413,101 | 4/1922 | Cushing . |
| 1,448,305 | 3/1923 | Langbein . |
| 1,495,675 | 5/1924 | Colt . |

(List continued on next page.)

FOREIGN PATENT DOCUMENTS

| | | |
|---|---|---|
| 1630 798 | 2/1991 | U.S.S.R. . |
| 1042 743 | 9/1993 | U.S.S.R. . |

OTHER PUBLICATIONS

Copy of Stryker Maintenance Manual entitled "System II OrthoPower 90 Battery Powered Surgical Instruments"—For Use With: 298–92, 94, 96, 98. (Stryker Surgical Brochure 298–92–16 REV (Mar. 1986)).

Copies of pp. 2,3 and 5 of Stryker prior art brochure/catalog No. 1420 Standard Bone Saw Handpiece, 1100 Series saw blades, and No. 1470 Sagittal Plane bone saw with Series 1370 blades.

Sketch A.

Aloe Medical Instruments Gallbladder Retractor item B–1323 p. 115, @ 1965.

*Primary Examiner*—Michael H. Thaler
*Attorney, Agent, or Firm*—Flynn, Thiel, Boutell & Tanis, P.C.

[57] ABSTRACT

A powered medical handpiece including an oscillatingly driveable chuck, and a blade fixable on the chuck and oscillating driveable thereby at a small amplitude for cutting. The chuck comprises a platform, a holddown screw having an enlarged head surrounded by a frictionally engaged cup washer and a shank structure threaded down into a central portion of the platform. A set screw limits the extent of unthreading of the screw from the platform. The blade is plate-like and has a forward cutting portion and a rearward mounting portion. The rearward mounting portion comprises a key hole having locking structure at the small diameter end thereof for resisting unthreading of the screw from a tightened position clamping the blade atop the platform. The blade further has drive openings flanking the narrow portion of the key hole for receiving upstanding drive pins and guide pins fixed on the platform. A cap preferably overlies the chuck and rear portion of a blade fixed thereon, for example to act as a vacuum hood for suctioning of chips created by a cutting operation.

13 Claims, 8 Drawing Sheets

U.S. PATENT DOCUMENTS

| | | | |
|---|---|---|---|
| 1,808,239 | 6/1931 | Logan | 30/157 |
| 1,940,855 | 12/1933 | Friedman . | |
| 2,427,580 | 9/1947 | Stryker . | |
| 2,557,364 | 6/1951 | Treace . | |
| 2,582,511 | 1/1952 | Stryker . | |
| 2,604,130 | 7/1952 | Derby . | |
| 2,649,838 | 8/1953 | Krause et al. . | |
| 2,854,981 | 10/1958 | Morrison . | |
| 3,103,069 | 9/1963 | Gary . | |
| 3,542,097 | 11/1970 | Dudek . | |
| 3,554,197 | 1/1971 | Dobbie . | |
| 3,656,393 | 4/1972 | Goellner | 83/698.41 X |
| 3,678,934 | 7/1972 | Warfield et al. . | |
| 3,703,036 | 11/1972 | Karubian . | |
| 3,750,283 | 8/1973 | Hoffman . | |
| 3,823,473 | 7/1974 | Hoffman . | |
| 3,852,881 | 12/1974 | Treace . | |
| 3,863,339 | 2/1975 | Reaney et al. . | |
| 3,901,117 | 8/1975 | Hoffman . | |
| 3,905,105 | 9/1975 | Tuke . | |
| 3,905,374 | 9/1975 | Winter . | |
| 3,927,893 | 12/1975 | Dillon et al. . | |
| 3,943,934 | 3/1976 | Bent . | |
| 3,952,412 | 4/1976 | Rhodes . | |
| 3,964,163 | 6/1976 | Russo . | |
| 3,974,868 | 8/1976 | Derbyshire . | |
| 3,977,289 | 8/1976 | Tuke . | |
| 3,978,862 | 9/1976 | Morrison . | |
| 4,008,720 | 2/1977 | Brinckmann et al. . | |
| 4,020,555 | 5/1977 | Hedrick . | |
| 4,032,747 | 6/1977 | Kunz . | |
| 4,036,236 | 7/1977 | Rhodes, Jr. . | |
| 4,064,871 | 12/1977 | Reno . | |
| 4,106,181 | 8/1978 | Mattchen . | |
| 4,229,963 | 10/1980 | Savinov et al. . | |
| 4,233,737 | 11/1980 | Poehlmann . | |
| 4,252,121 | 2/1981 | Arnegger . | |
| 4,386,609 | 6/1983 | Mongeon . | |
| 4,470,196 | 9/1984 | Hoffman . | |
| 4,528,753 | 7/1985 | Kuhlmann et al. . | |
| 4,543,718 | 10/1985 | Duescher . | |
| 4,584,999 | 4/1986 | Arnegger . | |
| 4,617,930 | 10/1986 | Saunders . | |
| 4,637,391 | 1/1987 | Schlein . | |
| 4,646,440 | 3/1987 | Decker . | |
| 4,648,182 | 3/1987 | Hoffman . | |
| 4,676,001 | 6/1987 | Wagner . | |
| 4,694,542 | 9/1987 | Koppe | 24/30.5 S |
| 4,711,030 | 12/1987 | Ruston . | |
| 4,728,876 | 3/1988 | Mongeon et al. . | |
| 4,730,952 | 3/1988 | Wiley . | |
| 4,736,742 | 4/1988 | Alexson et al. . | |
| 4,739,557 | 4/1988 | Wagner . | |
| 4,768,504 | 9/1988 | Ender . | |
| 4,783,886 | 11/1988 | Koppe | 24/30.5 S |
| 4,819,334 | 4/1989 | Mongeon . | |
| 4,873,461 | 10/1989 | Brennan et al. . | |
| 4,891,884 | 1/1990 | Torbet . | |
| 4,899,443 | 2/1990 | Beermann . | |
| 4,920,646 | 5/1990 | Grant . | |
| 4,922,612 | 5/1990 | Greenwood . | |
| 5,122,142 | 6/1992 | Pascaloff . | |
| 5,133,728 | 7/1992 | Petersen | 30/351 X |
| 5,263,972 | 11/1993 | Evans et al. . | |
| 5,439,472 | 8/1995 | Evans et al. . | |

CHUCK AND BLADE FOR POWERED MEDICAL HANDPIECE

This is a division of application Ser. No. 08/326,043 filed Oct. 19, 1994, now U.S. Pat. No. 5,468,247, which is a continuation of application Ser. No. 08/067,740 filed May 26, 1993, abandoned.

FIELD OF THE INVENTION

This invention relates to a chuck and blade for a powered medical handpiece, and particularly suited for bone sawing or cast sawing.

BACKGROUND OF THE INVENTION

Powered medical handpieces in the past have been provided with chucks for oscillating driving of the blades, such as saw blades suitable for cast cutting, bone sawing or the like. One example is that shown in Treace expired U.S. Pat. No. 2,557,364, and which has been in production by the assignee of the present invention for several decades. The present invention results from a continuing effort to improve on such prior art devices.

Thus, the objects of this invention include the provision of chuck and blade apparatus of simple and inexpensive structure, in which the chuck and blade can be partly covered by a shroud-like cap on the handpiece to facilitate suction chip collection during cutting, in which the apparatus is capable of easy chucking and un-chucking of a blade, and wherein the chucked blade is positively entrapped by the chuck even with the clamping, or holddown, part of the chuck inadvertently left not fully tightened.

SUMMARY OF THE INVENTION

In one embodiment according to the invention, the blade includes a holddown opening which includes lock means to inhibit unintended loosening of the clamping means of the chuck.

Further objects and purposes of the invention will be apparent to persons acquainted with apparatus of this general type upon reading the following description and inspecting the accompanying drawings.

DETAILED DESCRIPTION

In the following description, for convenience in reference, the words "top", "bottom", "left", and "right" and derivatives thereof, are applied to structure, in its orientation shown in the drawings, which orientation may obviously be different during handling and use.

Figure 1:
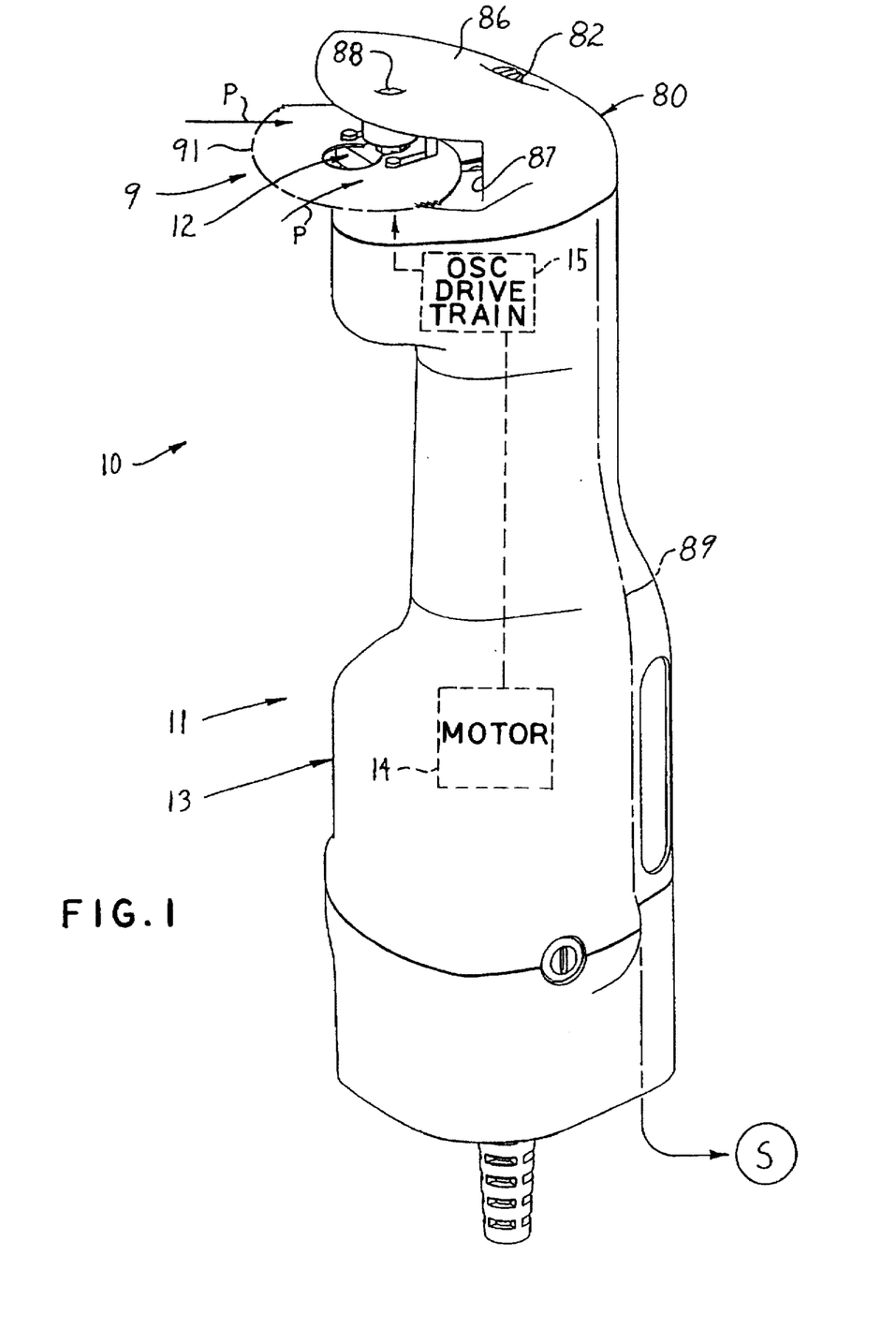
FIG. 1 is a pictorial view of a powered handpiece on which is installed a chuck and blade embodying the invention.
Figure 7:
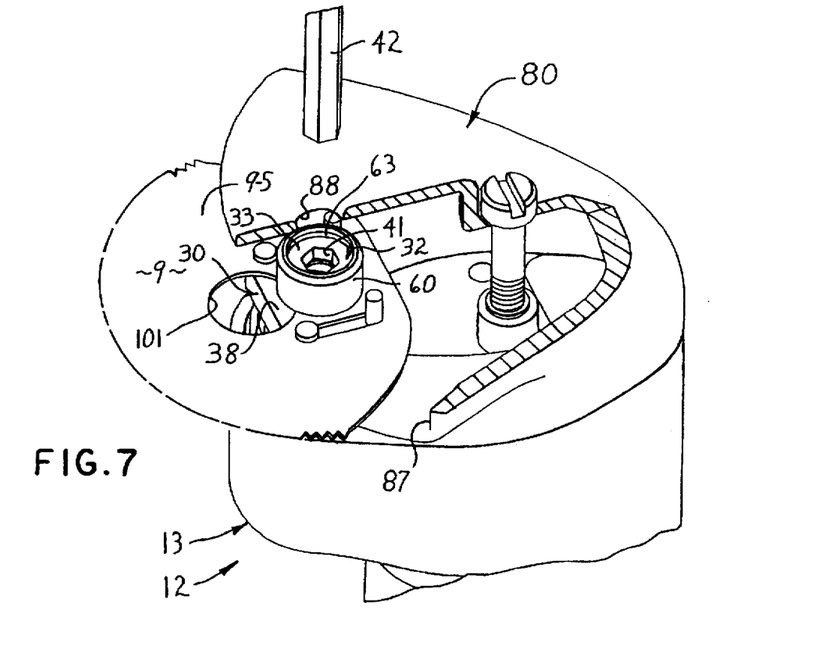
FIG. 7 is a pictorial view similar to FIG. 6 but with the blade fully installed on the chuck.

Turning to FIG. 1, a powered surgical apparatus 10, here for example a cast cutter, comprises a handpiece 11 mounting a chuck 12 at one end (the upper end in FIG. 1). FIG. 1 further shows a blade 9, here for example a toothed blade particularly intended for cutting through the thickness of a cast to facilitate removal thereof from a healed limb. Such blade 9 is shown in FIG. 7 in its fully mounted, normal operating position on the chuck 12 (in FIG. 1 the holddown screw, hereafter mentioned, is not tightened down). The handpiece 11 includes a housing 13 containing a drive system including a motor 14 driving an oscillating output drive train 15 for oscillating the input shaft 16 (FIG. 5) of the chuck 12. The motor 14 and oscillating drive train 15 may be conventional and of the known type discussed below and are schematically indicated in broken lines superpositioned on the top and bottom portions of the handpiece housing 13 in FIG. 1. The oscillating drive train 15, in the present example shown, is actuable to drive the chuck input shaft 16 (FIG. 5) in an oscillating manner as generally indicated by arrow A through a small arc about its longitudinal axis. Here the oscillating drive is applied to flats 20 on opposite sides of the shaft 16. The flats 20 receive, in pressfit thereon, a conventional oscillating yoke 17 (FIG. 10) which is a part of the oscillating drive train 15. Suitable sleeve bearings 22 and 23 fixed in the housing 13 support the shaft 16 for oscillating movement about its length axis within the housing 13 at its upper end portions 13A and 13B in FIG. 10. The chuck shaft 16 is prevented from axial movement in the housing 13 by any convenient means, here for example a down facing shoulder 24 and an up facing thrust ring 25.

High speed, low amplitude oscillating saw handpieces of the general kind above described have long been known. Examples of conventional oscillating saw handpieces of this general kind can be seen in a variety of prior art patents, for example U.S. Pat. Nos. 2,427,580 (Stryker), 2,557,364 (Treace) and 3,103,069 (Gary). The assignee of the present invention has for a number of years marketed an oscillating saw handpiece of this general kind as a cast cutter, for removal of surgical casts from broken limbs after healing, under the model designation 840, 841, 848, and 851 cast cutters. The circumferential stroke of such saws is typically quite small, for example, a stroke of approximately an ⅛ of an inch, measured along the peripheral of a saw blade having a radius of in the 1 to 2 inch range. The oscillating speeds are normally relatively high, for example 14,000 to 16,000 oscillations per minute. Handpieces of this kind are particularly suitable for sawing through casts on broken legs or arms in that the high speed allows fairly rapid cutting through the cast material whereas the small angular stroke prevents injury to skin by saw teeth in case the saw blade contacts the skin of the patient.

Figure 4:
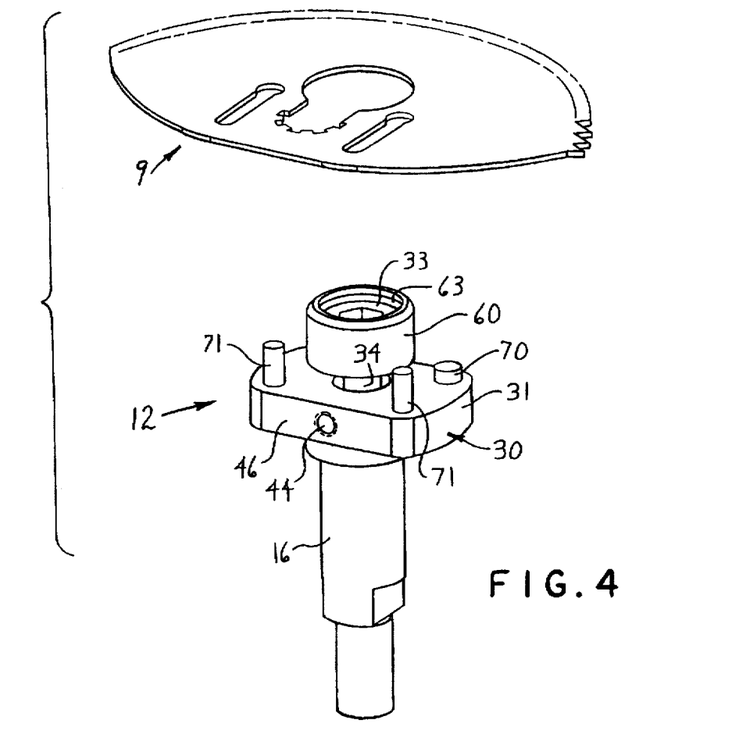
FIG. 4 is an exploded pictorial view of the chuck and blade of FIG. 1.

Turning now more particularly to the details of the present invention, the chuck 12 (FIGS. 4, 5, and 10) comprises a generally rectangular, block-like platform 30 fixed to and extending radially outward from the top of the shaft 16. The platform 30 and shaft 16 are conveniently a one-piece unit. In view of the oscillatory motion of the platform 30 in use, the longitudinal ends 31 of the platform 30 are preferably convexly curved as seen in FIG. 4. The platform 30 is preferably coaxial with a shaft 16.

A blade holddown screw 32 (FIG. 10) comprises an enlarged, substantially cylindrical head 33; a depending, coaxial, reduced diameter, nonthreaded cylindrical shank 34 beneath the head 33; and an externally threaded intermediate diameter subshank 35 depending coaxially from the shank 34. The head 33, shank 34 and subshank 35 are rigidly fixed together and may be of one piece. The reduced diameter of the shank 34, as compared to the subshank 35 and head 33, forms an annular groove 36 axially therebetween.

A preferably coaxial, internally threaded hole 37 extends down through the platform 30 (FIG. 10) and down into the shaft 16. The hole 37 threadedly receives the threaded sub-shank 35 of the holddown screw 32 and is of sufficient depth to enable loose reception therein of the unthreaded, reduced diameter shank 34. Indeed, the hole 37 is preferably of sufficient depth to enable the bottom 40 of the head 33 to be flush with the top face 38 of the platform 30. The top of the screwhead 33 is contoured for receiving a loosening and tightening tool of any desired type; in the present embodiment a hexagonal recess 41 in the top of the screwhead receives a conventional Allen wrench. A fragment of a suitable Allen wrench is shown in 42 in FIG. 2, prior to insertion into the hexagonal recess 41 of the screwhead 33. A set screw 44 (FIG. 10) threads into a threaded hole 45 which extends horizontally through the sidewall 46 of the platform into the threaded holddown screw hole 37. The reduced diameter inner end 47 of the set screw 44 is received in the annular groove 36 of the holddown screw 32, so as to prevent unintentional unthreading of the holddown screw 32 out of the top of the platform 30, by interference with an upward facing shoulder 50 where the holddown subshank 35 joins the shank 34. However, the set screw 44 permits threading of the holddown screw 32 between its up position shown in FIG. 10 and a down position with the bottom face 40 of the holddown screwhead 33 substantially flush with the top face 38 of the chuck platform 30.

In the embodiment shown, the bottom of the holddown screw 32 does not contact the top of the blade or the top face 38 of the chuck platform 30. Instead, for reasons hereafter discussed, the head 33 is recessed with a radial clearance fit, in an upwardly opening cup washer 60. The lower, central portion 59 of the holddown screwhead 33 is preferably stepped downward (FIG. 10) to extend down through a central opening 61 in the bottom 62 of the cup washer 60, leaving a down facing annular step face 58 of the screwhead 33 to abut the inside of the annular bottom 62 of the cup washer 60. The screwhead bottom 40 is flush with the bottom 62 of the cup washer 60. A resilient bowed, or wave-like, snap ring 63 is resiliently received in a radially inward facing annular groove 64 near the top of the peripheral wall 65 of the cup washer 60. The wave snap ring 63 resiliently bears down on the head 33 of the holddown screw 32 to positively entrap same within the cup washer 60. The cup washer 60 can rotate with the screwhead 33 during initial tightening of the screw, but the wave snap ring 63 allows the cup washer 60 to stop rotation with the screwhead 33 when finally tightened into contact with a blade 9, as hereafter more fully described.

Figure 2:
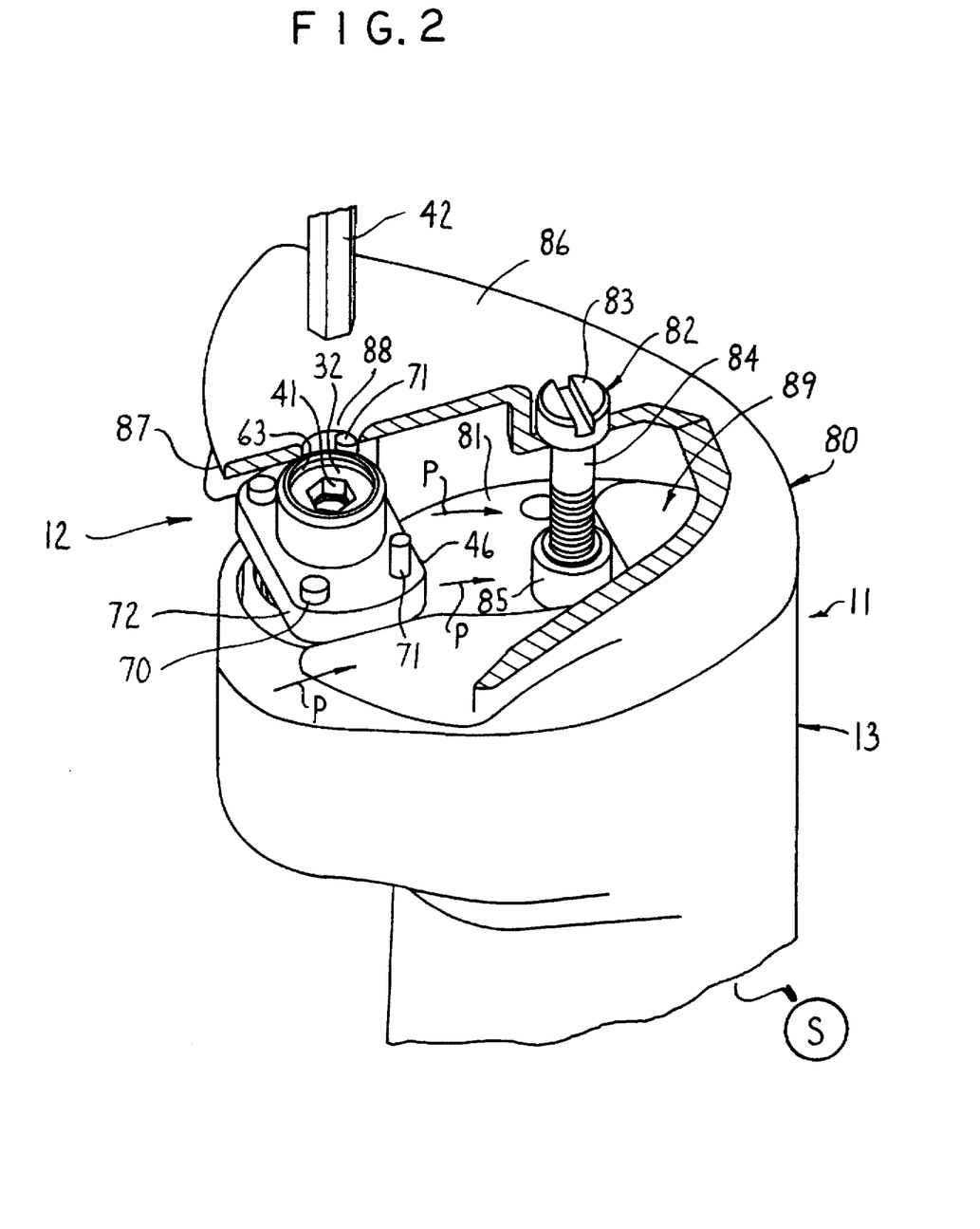
FIG. 2 is an enlarged, partially broken view of the upper end portion of FIG. 1 without a blade on a chuck.

Fixedly upstanding from the top face 38 of the chuck platform 30 are a pair of preferably identical drive pins 70, and a pair of preferably identical pilot, or guide, pins 71 which preferably also serve as drive pins. In the embodiment shown, the drive pins 70 are axially shorter but of larger diameter than the pilot pins 71. As seen in FIG. 2, the drive pins 70 are located close to the platform front wall 72, being spaced symmetrically on opposite sides of the cup washer 60. The pilot pins 71 are located close along the rear wall 46 of the chuck platform 30 in a symmetrical manner on opposite sides of the cup washer 60. The pins 70 and 71 are all located adjacent respective ones of the four corners of the top face 38 of the platform 30. As readily seen from the top in FIG. 9, each drive pin 70 is directly in front of a corresponding pilot pin 71 on a corresponding front/rear axis B1 or B2, the axes B1 and B2 being located symmetrically on opposite sides of the cup washer 60. All the pins 70 and 71 are spaced somewhat from the cup washer 60. As seen from the top in FIG. 9, each drive pin 70 is aligned with one of the pilot pins 71 on a diagonal axes B3 or B4 through the central axis of the holddown screw 32.

With the holddown screw 32 and cup washer 60 in their uppermost position generally shown in FIG. 10, the bottom 62 of the cup washer 60 is spaced somewhat below the tops of the pilot pins 71, but is spaced above the tops of the drive pins 70 by at least slightly more than the thickness of the blade 9. At the same time, the tops of the drive pins 70 are spaced above the top face 38 of the platform 30 by at least slightly more than the thickness of the blade 9. The tops of the pilot pins 71 are preferably no higher than the top of the cup washer 60 in the uppermost position of the holddown screw 32. These size relationships are selected to permit loading and unloading the blade with respect to the chuck in a manner hereafter described.

A hollow, downwardly concave cap 80 (FIGS. 1 and 2) is removeably fixed to the top wall 81 of the housing 13 (FIG. 1) by a screw 82. The screw 82 has a head 83 atop the cap 80 and a shank 84 (FIG. 2) extending down through a suitable hole in the top 86 of the cap 80 and threaded into a boss 85 fixed upon the top wall 81 of the housing 13. The cap 80 has a relatively wide, forward opening mouth 87, within which the chuck 12 is located and into which a blade 9 is insertable to be loaded into the chuck. The mouth 87 is wide enough to provide the blade 9 with substantial clearance during oscillation of the blade by the chuck. The height of the mouth is sufficient to enable insertion of a blade 9 over the top of the cup washer 60 as hereafter described and as schematically indicated in FIG. 10.

A hole 88 in the top 86 of the cap 80 is coaxially aligned above the head of the holddown screw 32 and is of diameter sufficient to loosely admit the Allen screw 42 downward therethrough into contact with the head of the holddown screw 32 for loosening and tightening same.

The presence of the cap 80 on top of the handpiece housing 13 is beneficial for several reasons. First, it shields the chuck 12, and the portion of the blade 9 mounted on the chuck platform 30, against accidental contact by the doctor or patient. Further, the handpiece housing 13 may, if desired, incorporate a suction channel 89 (FIGS. 1 and 2) opening through the top wall 81 of the housing 13 into the cavity beneath the downwardly convex cap 80 and connectible to a conventional external suction source (vacuum cleaner) S (FIG. 1). The mouth 87 then serves as a kind of vacuum cleaner intake for ingesting air entrained dust and chips resulting from sawing of a cast by the teeth of the blade 9. Arrows P in FIGS. 1 and 2 indicate schematically the flow of sawdust-particle-entraining air into the mouth 87 of the cover 80 and then into the suction channel 89.

The cap 80 can be removed from the top of the handpiece housing 13 by simply removing the screw 82 and then lifting cap 80 off the top wall 81 of the housing 13.

The blade 9 (FIG. 3) is preferably formed as a metal plate having a cutting edge, here provided with conventional saw teeth 91. The teeth 91 here are provided at the blade front edge 92 which lies, in use, just outside the mouth 87 of the cap 80, as illustrated in FIGS. 1 and 7.

Mounting means 93 (FIG. 3) are provided in a generally central portion of the blade 9. The mounting means 93 include a holddown through opening 100, substantially of key-hole shape and comprising a relatively large diameter, circular, front end portion 101 from which rearwardly extends a relatively smaller diameter, rear end portion 102 in the form of a rearwardly extending notch 102. The edge of the notch 102 is provided with lock means 103. In the preferred embodiment shown, the lock means 103 are an alternating series of substantially rectangular shaped, alternating tabs 104 and recesses 105 (FIG. 3A). The tabs 104 are twisted slightly out of plane as seen in FIGS. 3A and 3B, in a lock-washer like manner, to each provide an edge 106 (FIG. 3B) upset slightly above the face 107 of the blade 9 and angled slightly off perpendicular to the face 107 of the blade 9 in a direction to tend to prevent unthreading (here counter-clockwise) rotation of an overlying holddown member, here the cup washer 60, by digging slightly into the opposed surface thereof. In particular, the tabs 104 are twisted to provide the sawtooth effect seen in FIG. 3B, so that a tightening screwhead slides easily on a shallow ramp 108, but a loosening screwhead is balked by the steep edge 106.

With a sawblade 9 fully in place on the top face 38 of the chuck platform 30, as hereafter described, tightening of the holddown screw 32 proceeds as follows. At first, the cup washer 60, as a above-mentioned, rotates with the holddown screwhead 33. Eventually, the bottom 62 of the cup washer 60 contacts and begins to bear down against the blade tabs 104. The cup washer 60 continues to rotate with the screwhead 33 only until the friction of the blade tabs 104 thereon is strong enough to stop further cup washer rotation. This allows further tightening of the screw to be carried out, and thus greater clamping force to be applied to the blade 9 without damaging (e.g. scrubbing) of the blade tabs 104. Final tightening of the holddown screw 32 causes the bottom of the cup washer 60 to resiliently press down the tabs 104 of the blade 9.

Accidental loosening of the screw 32 is resisted by chisel-like edges 106 of the blade tabs 104 which tend to dig into the bottom of the cup washer 60 and prevent its loosening rotation. Intentional loosening of the screw 32 requires a substantial initial loosening of the screw, given torque exerted on the screwhead, sufficient to overcome the frictional angular coupling of the screw face 58 and cup washer 60, due to the bowed snap ring 63, thereby allowing the screw 32 to rotate slightly with respect to the cup washer 60 and substantially reduce the clamping force on the blade by the cup washer 60, without rotation of the cup washer with respect to the blade tabs 104. The cup washer need not rotate with respect to the blade tabs 104 until no longer effectively clamping the blade 9. This allows intentional loosening of the holddown screw 32 without damaging the blade tabs 104.

In the embodiment shown, the tabs and notches each have a circumferential width angle of about 22.5 degrees with a diameter across the free ends of diametrally opposed tabs of about 0.265 inch and a diameter across diametrically opposed notches of about 0.330 inch and with the tabs twisted out of plane to protrude beyond the plane of the blade about 0.002 inch to 0.006 inch on each side of the blade.

Figure 9:
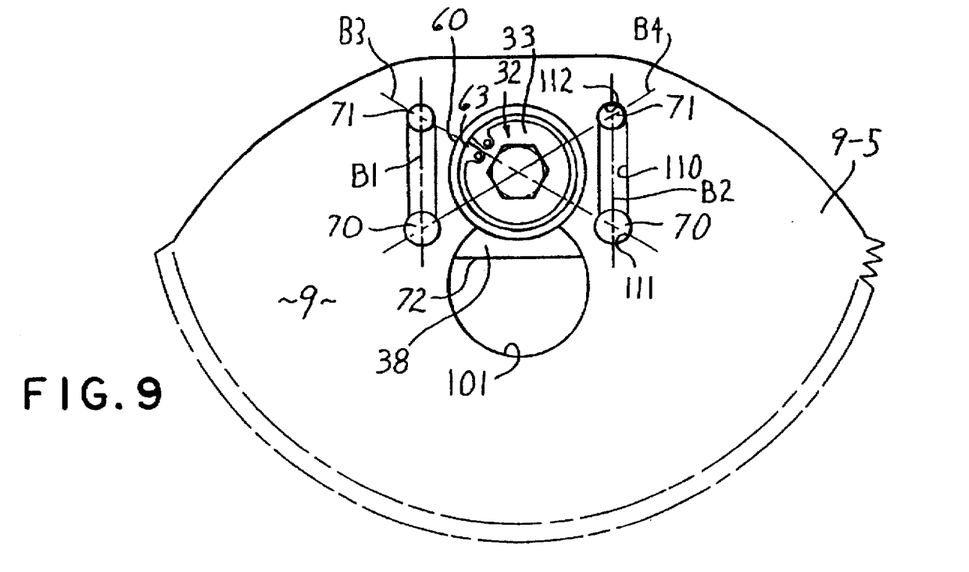
FIG. 9 is a plan view of a blade fully installed on the chuck, in its condition of FIG. 7.

The blade 9 further includes a pair of drive openings 110 (FIG. 3) spaced on opposite sides of the rear end portion 102 of the holddown opening 100. The drive openings 110 each comprise a front end drive portion 111 and a rear guide end portion 112. The end portions 111 and 112 of the openings 110 are sized and located with respect to the axis of the rear end portion 102 of the holddown opening 100 to receive therethrough the drive pins 70 and pilot pins 71, respectively, of the chuck 12 with the holddown screw 32 co-axial with holddown opening narrow rear end portion 102 of the blade 9. Such, for example is seen in FIGS. 7 and 9, namely in the fully installed position of the blade 9 on the chuck 12.

In the preferred embodiment shown, the drive openings 110 are closed and have an elongated key-hole shape, with the forward, drive end portions 111 being of larger diameter than the width of the remainder of the corresponding drive opening 110. This is in correspondence to the drive pins 70 being of larger diameter than the pilot pins 71, in the preferred embodiment shown. In the preferred embodiment shown, the drive openings 110 are sized to easily drop over the pins 70 and 71 of the chuck 12 but yet have at least the drive pins 70 snugly fit in the drive end portions 111 of the drive openings 110 so that oscillation of the chuck 12 (FIGS. 7 and 9) correspondingly oscillates the blade 9 in its own plane without significant lost motion and clatter.

In the preferred embodiment shown, in correspondence to the location of the pins 70 and 71 with respect to the holddown screw 32 of the chuck 12, the drive openings 110 in the blade have their length axes parallel to the length axis of the holddown opening 100 and spaced identically on opposite sides thereof. Further, the centers of the rounded drive opening end portions 111 and 112 are spaced evenly in front of and in back of, respectively, the axis of the rear-end portion 102 of the holddown opening 100, so that a straight line through the centers of one drive end portion 111, through the center of the guide end portion 112 of the other drive opening 110, passes through the axis of the rear end portion 102 of the holddown opening 100. In the particular blade 9 shown in FIG. 3, a small niche 113 appears in the perimeter of each drive opening 110. The niche 113 and its location along the perimeter of the opening 110, are optional. The niche 113, merely represents a convenient starting point for a laser, if the blade 9 is produced by laser cutting from metal sheet stock. Blades 9 can instead be produced by other methods, for example stamping.

Figure 3:
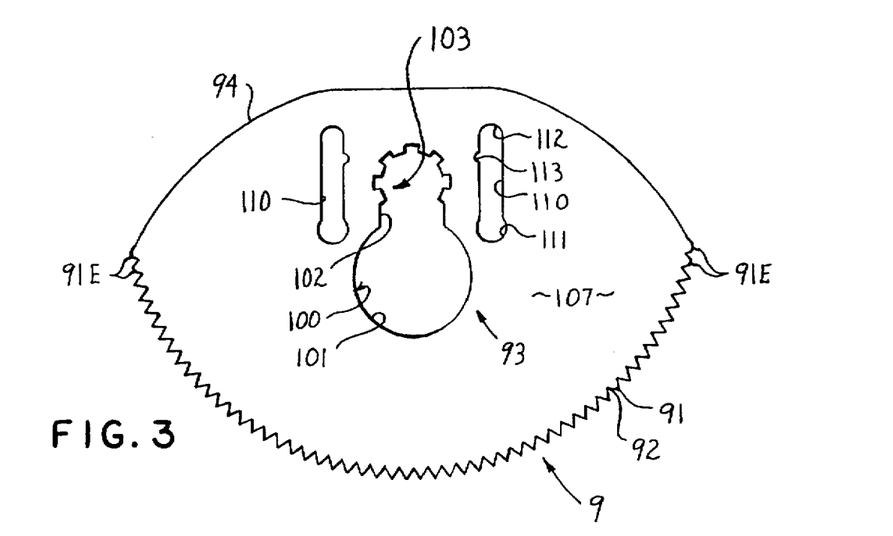
FIG. 3 is an enlarged plan view of a blade embodying the invention.
Figures 3A, 3B:
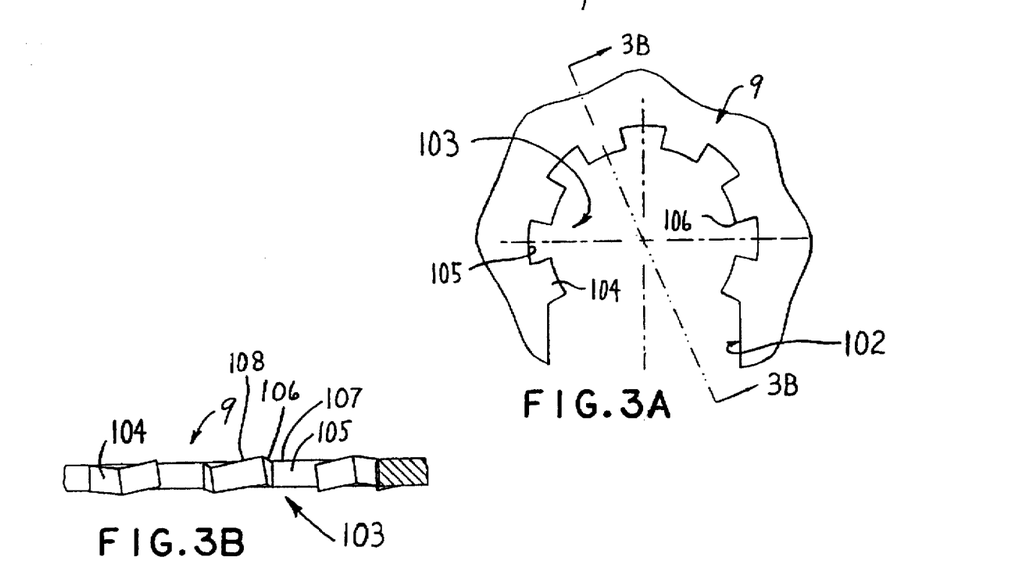
FIG. 3A is an enlargement of a portion of FIG. 3.
FIG. 3B is a fragmentary view substantially taken on the line 3B—3B of FIG. 3A.

In the preferred embodiment shown, the perimeter of the blade 9 is substantially football shaped, as seen in FIG. 3, the saw teeth 91 being along the convexly rounded front edge 92 of the blade and the mounting means 93 being spaced inboard therefrom and closer to the convex rear length edge 94 of the blade. The blade 9 may be of any desired material suitable for blade, particularly saw blade use. As shown for example in FIGS. 3–5, 8 and 9, the endmost tooth or two may be somewhat rounded, as indicated at 91E in FIG. 3, to provide the toothed edge of the blade with a somewhat less aggressive appearance at the ends thereof.

OPERATION

With the chuck 12 fully assembled and installed on the handpiece 11, in the manner shown in the drawings and with the cap 80 installed atop the handpiece housing 13 as shown in FIG. 1, a blade 9 may be installed on the chuck 12 as follows.

First, the wrench 42 (FIG. 2) is inserted downward through the hole 88 in the cap 80 into the hexagonal recess 41 in the head of the holddown screw 32. The holddown screw 32 is then rotated to thread it upward to its upwardmost position shown in FIGS. 6 and 10, as determined by the interference of the set screw 44 with the upward facing shoulder 50 (FIG. 10) atop the threaded sub shank 35 of the holddown screw 32.

Figures 10, 10A, 10B:
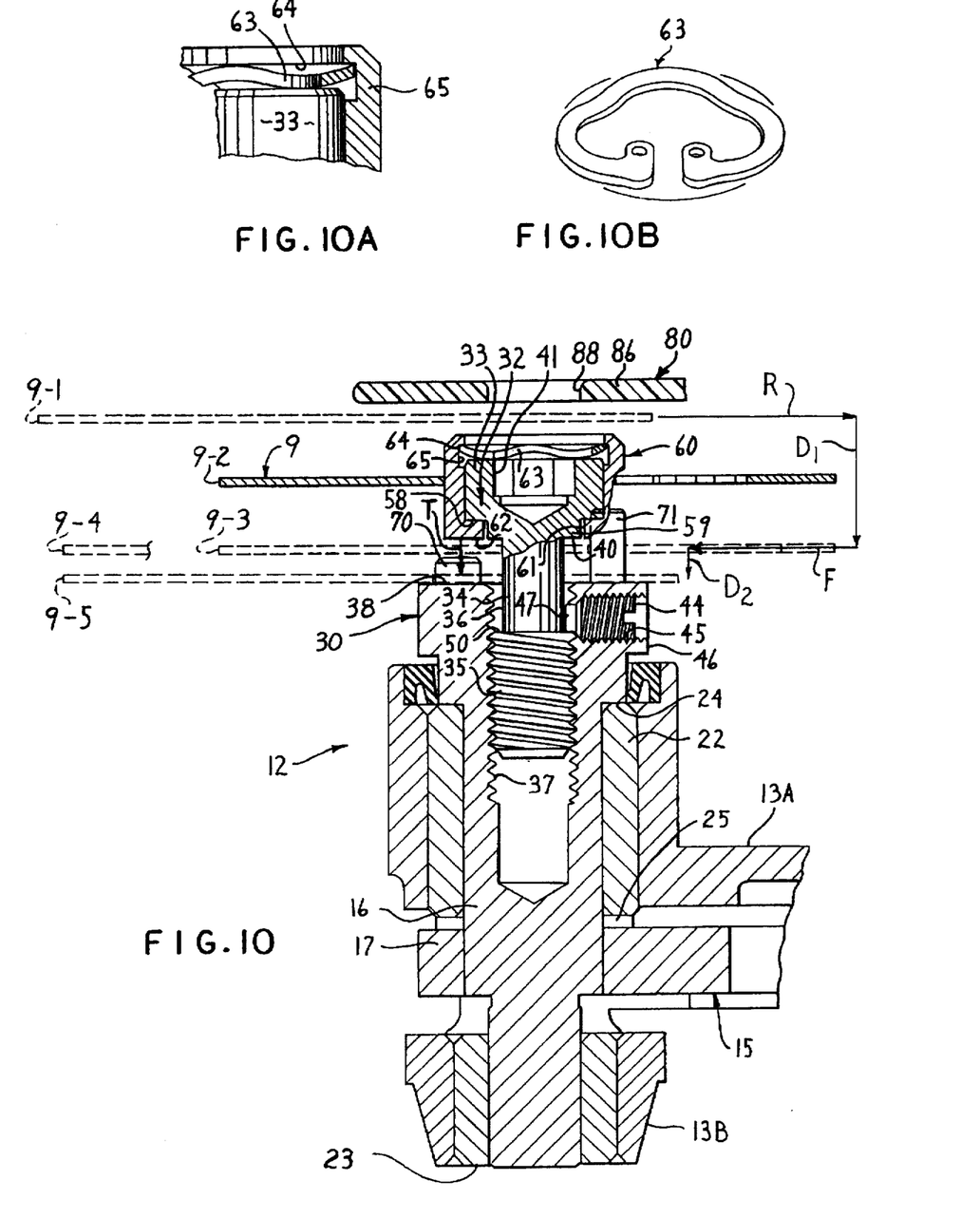
FIG. 10 is an enlarged, fragmentary, partially broken, central cross-sectional view of the chuck of FIG. 1, and substantially as taken on the cutting line 10—10 of FIG. 8, with a sequence of blade positions during installation on the chuck being variously shown in dotted and solid lines.
FIG. 10A is an enlarged fragment of FIG. 10.
FIG. 10B is an enlarged pictorial view of the wave snap ring of FIG. 10.

The blade 9 is then slid, rear edge 94 first, rearwardly (in the direction of the arrow R) into the gap between the top of the cup washer 60 and the underside of the cap 80, as indicated in broken lines at 9-1 in FIG. 10.

Sufficient space is left vertically between the top of the cup washer 60, in its uppermost position shown in FIG. 10, and the bottom of the cap 80 as to allow easy insertion of the blade 9 therebetween.

Figure 5:
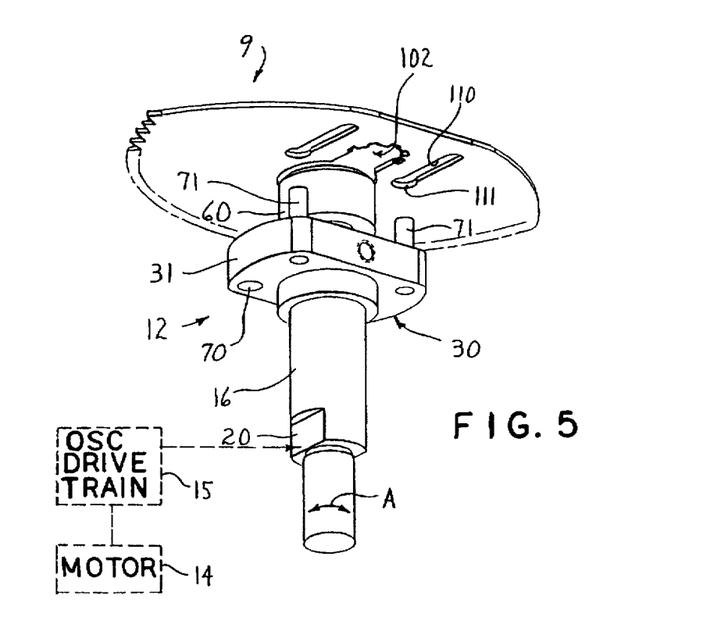
FIG. 5 is a further exploded view of the chuck and blade of FIG. 1 taken from a different angle as compared to FIG. 4.

With the large diameter, front-end portion 101 of the holddown opening 100 located coaxially above the cup washer 60 and the wide, drive end portions 111 of the drive openings 110 located above respective ones of the pilot pins 71, as seen in FIG. 5, the blade 9 can be dropped downward through its position shown at 9-2 in FIG. 10, in which the large diameter front end portion 101 of the holddown opening 100 snugly, but freely vertically slidably, receives the cup washer 60 therethrough. Downward dropping of the blade 9 continues, in the direction of the arrow D-1, to the blade position indicated in the dotted lines at 9-3 in FIG. 10 and shown in solid lines in FIGS. 6 and 8, in which the blade 9 rests atop the relatively short drive pins 70 and receives the taller, narrower, pilot pins 71 upward through the wider forward end portion 111 of the drive openings 110.

The relatively large size of the cup washer 60 and the holddown hole front end portion 101 facilitates finding the cup washer 60 coaxially with the hold portion 101. The greater width of the front, drive end portions 111 of the drive openings 110, to slidingly fit over the wider diameter drive pins 70, facilitates finding of the tops of the narrower, taller guide pins 71 therewith, since the forward, drive ends 111 of the drive holes 110 are noticeably larger in diameter than the narrow guide pins 71.

Whereas some side to side movement of the blade 9 may be necessary, as it is moved rearward in the direction of the arrow R, prior to dropping down over the cup washer 60 (from position 9-1 to position 9-2 in FIG. 10), mere pivoting of the blade 9 around the axis of the cup washer 60 will suffice (without horizontal shifting front to rear or side to side) to engage the guide pin 71 with the large, drive end portions 111 of the drive openings 110.

After the blade has dropped down to its position 9-3 of FIG. 10, one simply pulls the blade forward, in the direction of arrow F, until the large diameter, front, drive end portions 111 of the drive openings 110 drop down (see arrow D-2 in FIG. 10) over the relatively large diameter, short, drive pins 70. See the blade drop from blade position 9-4 to 9-5 in FIG. 10. This forward blade movement, in the direction of the arrow F in FIG. 10, is the FIG. 8 to FIG. 9 blade position shift, in which the blade slides forward above top face 38 of the platform 30, with the wide front end portion 101 of the holddown opening 100 sliding forward out of coaxial alignment with the holddown screw 32 and cup washer 60 to bring the narrower rear end portion 102 of the holddown opening 100 into coaxial alignment around the narrow diameter central shank 34 of the holddown screw 32. This is the final, installed position 9-5 of the blade 9 on the chuck 12.

Figure 6:
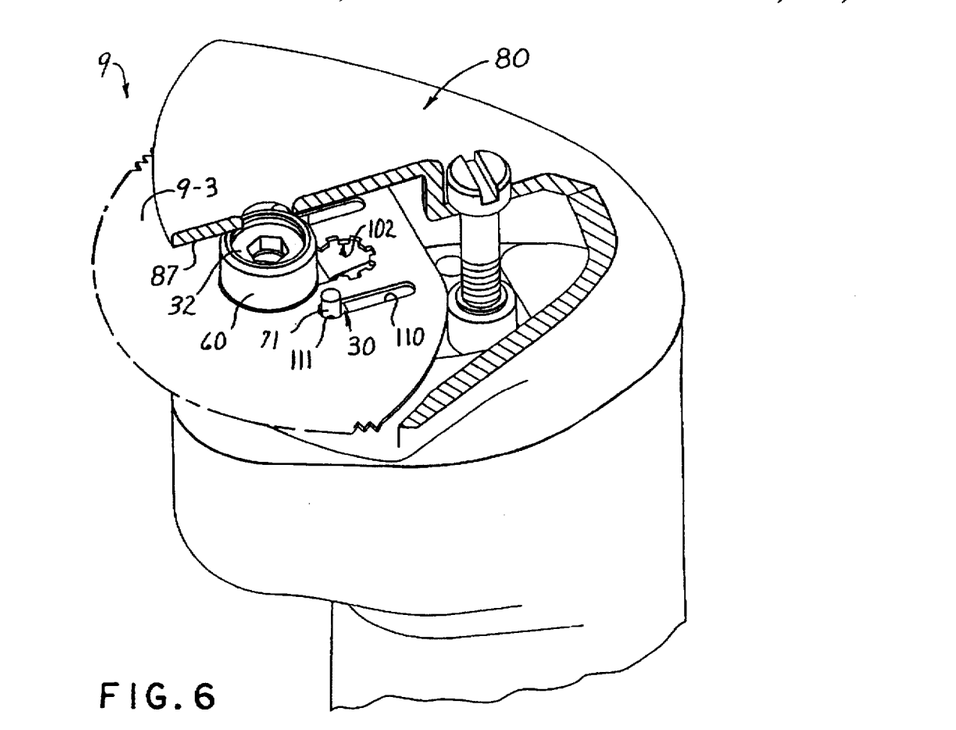
FIG. 6 is a pictorial view similar to FIG. 2 but with a blade partly installed on the chuck.
Figure 8:
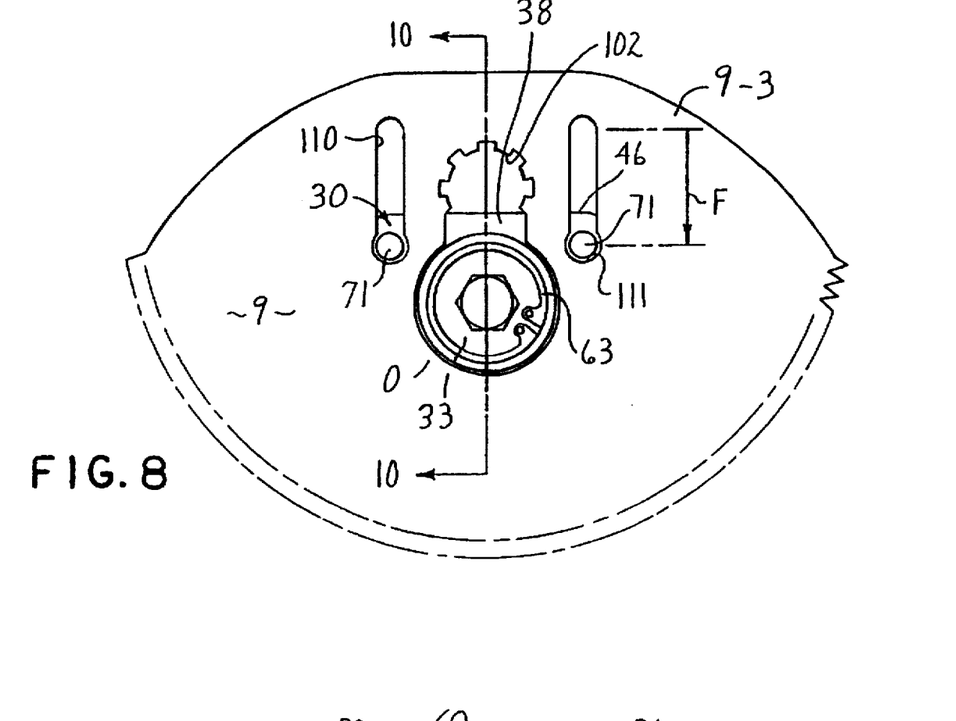
FIG. 8 is a plan view of a blade partly installed on the chuck in its condition of FIG. 6.

By maintaining the cup washer 60 axially fixed on the screwhead 33 (here by means of the wave snap ring 63), the cup washer 60 cannot drop down from the raised (FIG. 10) screwhead 33 and block forward movement (see arrow F) of the blade, along the top of the short drive pins 70, from its FIG. 6, 8 position to its FIG. 7, 9 position.

To retain the blade in its installed position 9-5 on the chuck, the wrench 42 is inserted downward through the hole 88 in the cap 80 of the handpiece to fit down into the hexagonal recess 41 in the head 33 of the holddown screw 32. The wrench 42 is then rotated in a direction to tighten down the holddown screw 32, along the path marked by the arrow T in FIG. 10, until the bottom 62 of the cup washer 60 rests atop and presses down on the portion of the blade 9 surrounding the rear end portion 102 of the holddown opening 100. This leaves the parts in their position of FIG. 7 and rigidly fixes the blade 9 on top of the platform 30 of the chuck 12. As the bottom face 62 of the cup washer 60 bears down on the top of the blade tabs 104, the latter flatten out of their slightly tilted condition shown in FIG. 3B so that the bottom face 62 of the cup washer 60 bears down in substantially continuous area wise fashion on the portion of the top surface of the blade that it overlays. Tightening of the bottom 62 of the cup washer 60 down against the sharp, uptilted edges 106 (FIG. 3B) of the tabs 104 (FIGS. 3A and 3B) of the rear end portion 102 of the holddown opening 100 of the blade causes those sharp edges 106 to resist untightening rotation of the cup washer 60 by biting slightly into the underside 62 thereof, in the manner of a lock washer. At the same time, the holddown screwhead 33 resists rotation with respect to the cup washer 60 by reason of firm frictional engagement therebetween provided by the axial pressure of the screwhead on the cup washer (FIG. 10). In this way, the holddown screw 32 is effectively locked against loosening once it has been tightened, and despite vibration or other disturbances, during energization of the handpiece and cutting by the blade, as might otherwise tend to loosen the holddown screw 32.

To remove the blade 9 from the chuck 12, the wrench 42 (FIG. 7) is once again inserted down through the hole 88 in the cap 80 and into the hexagonal recess 41 in the top of the holddown screw 32 and is rotated in the opposite (loosening) direction. The bite of the upturned edges 106 of the tabs 104 (FIGS. 3A and 3B) of the blade 9 against the bottom face 62 of the cup washer 60 tends to resist rotation of the cup washer in the screw loosening direction. Sufficient twisting force on the wrench 42 overcomes the circumferential friction between the holddown screwhead 33 and the interior of the cup washer 60 and wave snap ring 63. Thus, the wrench 42 can carry out an initial rotation of the holddown screw 32 in the loosening direction, even though the cup washer 60 is initially held fixed by the tab edges 106 of the blade. However, once initial screw loosening has relieved the downward pressure of the cup washer on the blade tab edges 106, the bottom face 62 of the cup washer 60 is no longer gripped by the upsprung tab edges 106, and the cup washer 60 is free to rotate in the loosening direction with the screw 32. Thus during the first portion of loosening rotation of the screw, it is not necessary to circumferentially scrub the bottom of the holddown screw, or surrounding cup washer, against the upturned tab edges 106. Accordingly, this avoids marring the bottom of the screwhead and cup washer, so that the same can be used repeatedly with many successive blades, over a long period of time without marring. At the same time the edges 106 of the tabs 104 on the blade are not dulled or distorted or otherwise made unserviceable upon first loosening of the holddown screw.

Indeed, inclusion of the cup washer 60 and ability of the screw 32 to rotate in initial loosening with respect to the cup washer reduces the circumferential shearing load on the locking tabs 104 during initial loosening rotation of the holddown screw, thereby avoiding circumferential shearing of a tab 104. In this way, it is possible to reliably chuck the same blade several times, as when the user may decide to alternate between different first and second blades for different cast, or other, cutting operations.

Removal of the blade 9 from the chuck 12 is by reversal of the abovestated installation steps, namely by loosening the screw 32 fully, to the extent permitted by the set screw 44, lifting the blade to above the short drive pins 70, pushing the blade rearwardly to the extent permitted by the tall guide pins 71, raising the blade upward along the guide pins 71 and past the cup washer 60 and then sliding the blade forwardly out from between the top of the cup washer 60 and the bottom of the handpiece cap 80.

By providing the lock means 103 integrally within the blade 9, several problems are avoided.

For example, in high frequency oscillating surgical and medical saws, for carrying out medical procedures such as cast cutting and bone sawing, using a conventional blade without a lock washer between the head of the holddown screw and the opposed support face of the chuck, risks loosening of the holddown screw during use. At best the user may notice the loosening and stop the medical procedure to tighten the holddown screw. However, in some prior designs, such loosening might risk escape of the blade from the chuck during oscillation. Throwing of a blade from a high speed oscillating chuck may be dangerous to personnel nearby. In the present invention, inclusion of the lock means 103 on the blade can avoid such loosening of the screw during use.

Further, inclusion of the lock means 103 on the blade avoids the need for a separate lock washer between the holddown screw and blade. This is desireable since it avoids the need for an extra piece and the risk of loosening such extra piece during changing of blades.

Further, a conventional lock washer floating loose on the shank 34 of the screw, between the screwhead 33 and the top 38 of the chuck platform 30, would get in the way while the blade is attempting to be installed. More particularly, with the apparatus in its attitude of FIG. 10, gravity would cause such a lock washer to lie spaced down from the screwhead and atop the chuck platform 30, in the way of final positioning of a blade atop the chuck platform. Thus, the separate lock washer would somehow have to be held up by the user against the bottom of the set screwhead while the blade was being transferred down from its position 9-3 to its position 9-4, difficult to do because of inadequate room for one's fingers with the blade in the narrow confines between the holddown screwhead 33 and the top of the chuck platform 30. Alternatively the structure would have to be turned up-side-down, again making installation of the blade cumbersome.

Elimination of a conventional lock washer advantageously eliminates the eventual wearing out, and need to replace, such a lock washer after repeated chuckings of a series of blades. Such replacement would require removal of the cap 80, loosening of the set screw 44, and removal of the and holddown screw 32 and subsequent reassembly with a new lock washer in place.

Indeed, the extra time and effort required to disassemble the apparatus and replace a conventional lock washer would tend to cause the user to put off replacing even a no longer safe lock washer.

While the broader sense of the present invention, contemplates some variation in the locking means 103, the tabs 104 and intervening recesses 105 seen in FIGS. 3 and 3B can be easily formed, with the rest of the blade, in a single stamping operation. Alternately, the tabs 104 and recesses 105 can also be formed with the rest of the blade in a single laser cutting operation, followed by a simple upsetting operation to twist the tabs 104 to provide the locking edges 106 above and below the plane of the blade as seen in FIG. 3B. In both types of manufacturing a number of blades can be cut from a single sheet of uniform thickness sheet metal so that the blade consists merely of a single piece of sheet metal stock with no need to add an extra piece for locking.

The saw teeth can be conventionally hardened. The tabs 104 can be hardened to the same extent, a lesser extent or not at all, depending on the hardness of the basic sheet metal stock.

During cutting, the handpiece is usually held with its length axis generally horizontal and the blade cutting edge 91 generally downward, rather as in the orientation of FIGS. 3, 8 and 9, as if FIGS. 1, 6, and 7 were rotated about 90 degrees counterclockwise. In this position, if the holddown screw 32 and pins 70 and 71 were absent, the blade 9, by gravity, would tend to fall downward out of the mouth 87 of the cover 80. However, under the present invention, the holddown screw 32, cup washer 60, and pins 70 and 71 act also as safety devices to interfere with accidental dropping or throwing of the blade 9 out of the mouth 87 of the cover, particularly during oscillation of the chuck 30. For example, assuming that the user has forgotten to fully tighten screw 32 after installing a blade 9, turning on the handpiece motor 14 to oscillate the chuck 12 may allow the blade to float away from the top face 38 of the chuck platform 30. However, with the bottom of the cup washer 60 less than a blade thickness from the top face 38 of the chuck platform 30 the blade 9 cannot escape from the short drive pins 70 and so cannot drop or be thrown from the handpiece.

Further, if the user has left the holddown screw 32 even looser, the blade 9 can shift axially beyond the top of the short drive pins 70, to its position 9-4 (FIG. 10), however, gravity would simply cause the blade to "hang" in that position 9-4, on the elongated pilot pins 71, the blade being trapped against movement axially further away from the platform 30 by the bottom 62 of the cup washer 60 interfering with tabs 104 (FIG. 3A) and the portion of the blade 9 surrounding the tabs 104. Thus, the blade is blocked by the pilot pins 71 and slim shank 34 of the holddown screw 32 from being thrown or falling from the mouth 87 of the handpiece. If the handpiece motor 14 is energized in this condition, the user is warned of the loose condition of the holddown screw 32 by the tendency of the loose blade 9 to flap and clatter noisily against the tops of the drive pins 70 and the bottom face 62 of the cup washer 60.

However, it is unlikely that the user will forget to tighten the holddown screw 32 because he will, upon inserting of the blade 9 fully to its position 9-5 in FIG. 10, notice that the blade is still free to flop about axially, a forcible hint that the blade installation must yet be completed by tightening of the screw 32.

It is unlikely that the user would fail to complete movement of the blade 9, during installation, through its positions 9-1 to 9-5, because at all of the intermediate blade positions 9-1 through 9-4, the looseness and position of the blade with respect to the chuck platform 30 and pins 70, 71 and cup washer 60 provide tactile and visual cues to the user that blade installation is not yet complete.

Removal of the screw 82 (FIG. 2) allows the cover 80 to be removed from the end of the handpiece housing 13. Absent the cover 80, the blade 9 may be lowered onto the chuck 12 (in its upfacing position of FIG. 5) without the above-described rearward translation of the direction of arrow R in FIG. 10, whereafter movement of the blade into its final position with respect to the chuck can be carried out by the above discussed movements through the directions of the arrows D1, F and D2 as above described with respect to FIG. 10. While the disclosed apparatus can be used without the cover 80 in place, this is not recommended because it undesireably leaves the rear portion of the blade uncovered and eliminates suctioning of dust and particles away from the cutting/sawing site.

MODIFICATIONS

Figure 11:
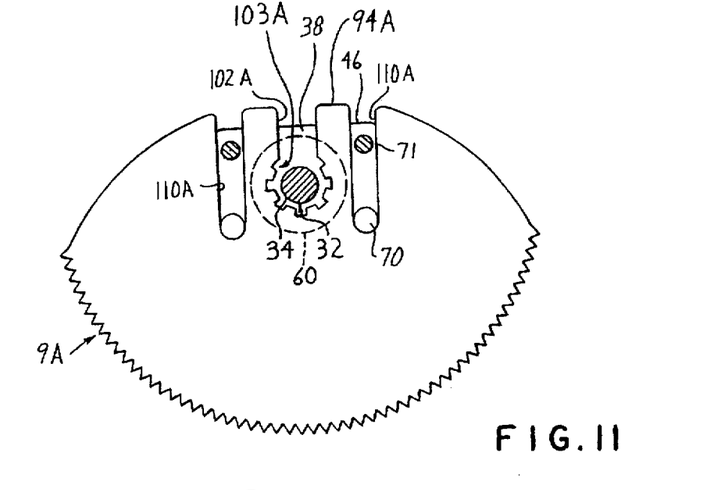
FIG. 11 is a plan view generally similar to FIG. 9 but showing a first modification blade.

FIG. 11 shows a blade 9A modified to simplify its installation in the chuck by allowing it to be merely slide rearwardly onto and along the top face of the chuck platform 30 beneath the raised (as in FIG. 10) holddown screwhead 33 and cup washer 60, thereby eliminating the need for movement of the blade in the directions of the arrows D1, F and D2 discussed above with respect to FIG. 10, during chucking of the blade. To this end, the holddown opening 102A and the drive openings 110A in the modified blade 9A are extended rearward to open notch-like through the rear edge 94A of the blade. Further, the drive notches 110A are widened throughout their length to clear the front mounted, wide drive pins 70. Further, the wide diameter front end portion 101 of the preferred blade 9 of FIGS. 1-10 is eliminated to avoid reduction in the number of tabs of the locking means 103A. Unfortunately, this modified blade 9A has several substantial disadvantages. For example, if the user fails to tighten the holddown screw 32 upon installation of the blade, or allows the holddown screw 32 to loosen in use, the modified blade 9A could simply fall or be thrown downward out of the chuck 12, since the rear opening notched holddown and drive openings 102A and 110A no longer have rear edges to block forward exiting of the blade 9A from the chuck and away from the holddown screw shank 34 and pins 70 and 71.

Also, the looseness of blade contact with the guide pins 71 and lack of blade contact with the rear portion of the drive pins 70 may increase wear of the blade material at the edge of the drive notches 110A or, if the blade is of relatively brittle material, may risk breakage of the blade 9A in that area, and could cause the blade 9A to damage the pins 70 and/or 71.

Hence, this modification blade 9A is considered to have substantial safety and other deficits and is thus not preferred.

Figure 12:
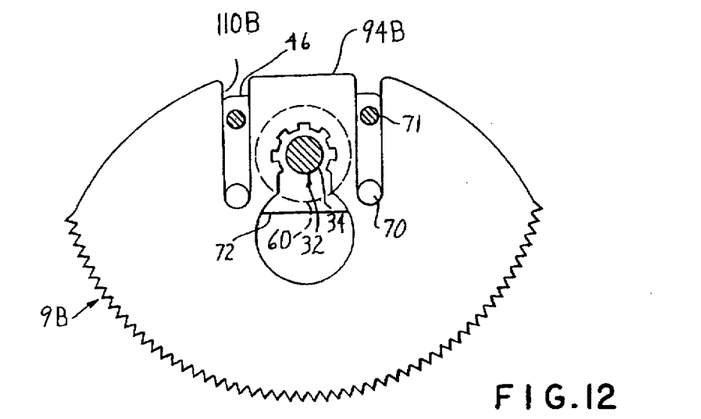
FIG. 12 is a plan view similar to FIG. 11 but showing a second modification blade.

FIG. 12 discloses a further modified blade 9B in which the drive openings 110B open rearward, notch-like, as in above discussed modification blade 9A, but wherein the guide opening remains closed to the rear and of the form generally shown above with respect to the preferred embodiment blade 9. However, the modified blade 9B cannot be simply slid rearward on the top of the platform 30 in a single motion chucking as in modification blade 9A above described, but instead must be installed by movement along the directions of arrows R, D1, F and D2 shown in FIG. 10 and discussed with respect to the preferred embodiment blade 9. Thus, the rearward opening, notch like, of the drive openings 110B does not ease installation of the blade 9B. Rather, same has the disadvantage of simply weakening the blade 9B along its rear edge portion 94B. The blade 9B also has the above-mentioned blade and/or pin damage problems of above discussed modification blade 9A. Accordingly, since this blade embodiment 9B has disadvantages, it too is not preferred.

Figure 13:
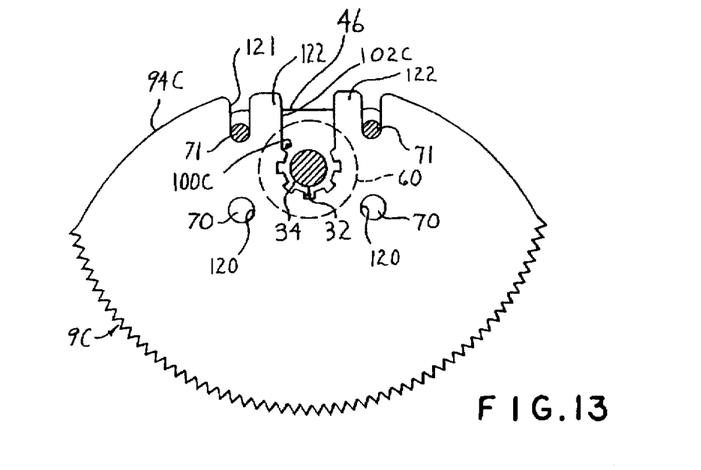
FIG. 13 is a plan view similar to FIG. 11 but showing a third modification blade.

FIG. 13 shows a further modified blade 9C which, like the modified 9A of FIG. 11, is insertable rearwardly into the chuck 12 between the raised (FIG. 10) cup washer 60 and the platform 30, with a rearward horizontal insertion motion. However, the modified blade 9C inserts rearwardly over the tops of the short, wide drive pins 70, into the position 9-4 of FIG. 10, after which the modified blade 9C can then drop in the direction of the arrow D2 in FIG. 10 onto the top 38 of the platform 30. To this end, the modified blade 9C eliminates the large diameter front end portion 101 of the holddown opening 100 of the preferred blade 9 of FIGS. 1-10. Instead, the rear end portion 102C of the holddown opening 100C is formed as a notch which opens rearward through the rear edge 94C of the blade. Further, in the modified blade 9C, each pin pair 70, 71 does not share an elongate drive opening, like the elongate drive opening 110 of the preferred blade 9 of FIGS. 1-10. Instead, each large diameter drive pin 70 is received through its own hole 120 in the modified blade 9C and each guide pin 71 is received in its own rear opening notch 121 in the modified blade 9C. However, the modified blade 9C has several disabilities which make it a nonpreferred embodiment.

For example, should the holddown screw 32 be sufficiently loose during operation, the blade 9C may rise or tilt toward and over the top of the short drive pins 70 and slide forward (downward in FIG. 13). The guide pins 71 and holddown screw 32 (more particularly the shank 34 thereof) cannot stop continued forward motion of the blade 9C over the top of the drive pins 70 since they are open through the rear edge of the blade through the rear opening notches 121 and 102C. Thus, much as above discussed with respect to the modified blade 9A, the modified 9C of FIG. 13 may escape, or worse yet be thrown, from the chuck 12 during operation, after failure to tighten holddown screw 32. In both FIG. 11 and FIG. 13, as the modified blades 9A and 9C slip further and further forward (downward in the drawings) from their proper drive location shown, the toothed forward edge of the blade gets farther and farther forward from the center of oscillation of the chuck (the axis of the holddown screw 32), so that the amplitude of oscillation of the teeth and the linear speed movement of the teeth increases, so as to be at maximum if the blade 9A or 9C leave the chuck 12 during oscillation of the chuck 12.

Further, the notching of the rear edge 94C of the blade by the central notch 102C and the flanking notches 121 leaves cantilevered tabs 122 which may have a tendency to flex or fatigue, and in any event weakens the rear edge portion of the blade, much as in the modified blade 9A of FIG. 11.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. A chuck for mounting on and oscillatory driving by a powered medical handpiece for oscillatory driving of blades, including cast cutter blades, said chuck comprising:

a platform for mounting on and oscillatory driving by a medical handpiece and having an exposed top face;

clamp means protruding from said platform top face and adjustable up and tightenable down with respect to said platform top face, said clamp means having radially enlarged head means adjustable toward and away from said platform top face for alternatively clamping a blade fixedly with respect to said platform and unclamping said blade from said platform;

drive means fixed with respect to and upstanding from said platform top face at a location radially offset from said clamp means and moveable through an arc upon oscillatory driving of said chuck by a powered medical handpiece, said upstanding drive means being engageable with a blade for oscillating same in response to oscillatory driving by a medical handpiece in which said clamp means comprises a screw having a shank threaded into said platform, said enlarged head means comprising an enlarged screwhead fixed on said shank and a cup washer coaxially surrounding and underlying said screwhead, the underside of at least said cup washer being engageable with a blade lying atop said platform for clamping a blade to said platform, means frictionally engaging said cup washer on said screwhead for (1) permitting the bottom of said cup washer to be fixed with respect to a blade and against rotation with said screw during initial loosening of said screw and (2) lifting and rotating said cup washer with said screw during final loosening of said screw, said means frictionally engaging said cup washer on said screwhead comprising a wave ring snugly overlying the top of said screwhead and fixed to an upper peripheral wall portion of said cup washer.

2. The apparatus of claim 1 in which said screw is captive on said platform and has a limited range of threaded movement with respect to said platform.

3. A chuck for mounting on and oscillatory driving by a powered medical handpiece for oscillatory driving of blades, including cast cutter blades, said chuck comprising:

a platform for mounting on and oscillatory driving by a medical handpiece and having an exposed top face;

clamp means protruding from said platform top face and adjustable up and tightenable down with respect to said platform top face, said clamp means having radially enlarged head means adjustable toward and away from said platform top face for alternatively clamping a blade fixedly with respect to said platform and unclamping said blade from said platform;

drive means fixed with respect to and upstanding from said platform top face at a location radially offset from said clamp means and moveable through an arc upon oscillatory driving of said chuck by a powered medical handpiece, said upstanding drive means being engageable with a blade for oscillating same in response to oscillatory driving by a medical handpiece;

guide pin means upstanding from said platform adjacent said head means, for controlling the lateral position of a blade as the latter drops past said head means, said drive means including drive pin means upstanding from said platform adjacent said head means for positive oscillatory driving of a blade, said guide pin means being taller than said drive pin means.

4. The apparatus of claim 3 in which the clamp means comprises a screw upstanding from a central portion of platform, said guide pin means comprising of a pair of guide pins at respective rear corner locations on said platform, said drive pin means comprising a pair of drive pins at respective front corner locations on said platform, said drive pins of being of diameter between that of said head means and guide pins.

5. The apparatus of claim 4 in which said screw is captive on said platform and has a limited range of threaded movement with respect to said platform.

6. The apparatus of claim 3 including means for limiting the maximum height to which said head means can rise above said platform, said guide pin means upstanding from said platform to a level above the highest level to which the bottom of said head means can rise above said platform, and controlling the lateral position of a blade as the latter drops past said maximum height of said head means, said drive pin means upstanding from said platform to a height about equal to the thickness of a blade to be chucked.

7. In combination, a powered medical handpiece, including an oscillating driveable chuck, and a blade removeably fixable on said chuck and oscillatingly driveable thereby at low amplitude for cutting hard material such as cast material or bone without harming adjacent soft tissue, said combination comprising:

a chuck comprising a platform, a holddown screw having enlarged head means and means defining a shank threaded into a central portion of said platform for varying the spacing of said head means above said platform, said screw shank having a diameter less than said head means and extending from said head means into said platform;

a plate-like blade having cutting means at least a front edge thereof for positioning in front of said chuck, mounting means for fixed mounting of said blade on said chuck and including a holddown opening having a first portion for initially receiving a portion of said screw with said blade in an intermediate position on said chuck, said holddown opening having a second portion communicating with said first portion in a manner to allow said blade to slide laterally along said platform with said screw shank shifting from said first portion to said second portion of said holddown opening, said second portion of said holddown opening having anti-rotation lock means engageable between said head means and platform for resisting unintended unthreading of said holddown screw from said platform.

8. The apparatus of claim 7 in which said lock means comprises tab means for lockingly engaging said head means, said tab means protruding into said second portion of said holddown opening, said tab means being upset from the surface of said blade for lockingly engaging said head means and inhibiting rotation thereof.

9. The apparatus of claim 7 in which said holddown opening is key-hole shaped, said first portion thereof being of diameter large enough to receive said head means axially therethrough and said second portion thereof being of substantially smaller diameter, less than that of said head means but greater than that of said shank, said lock means comprising tab means on said blade protruding into said smaller diameter portion of said holddown opeing for engaging said head means in a manner to inhibit unthreaded rotation of said holddown screw with respect to said platform.

10. The apparatus of claim 7 in which the platform has drive means adjacent its screw and engageable with drive opening means in said blade, said drive opening means in said blade being adjacent said holddown opening in said blade, said chuck including guide pin means upstanding from said platform adjacent of said head means and above the highest level of the bottom of said head means above said platform for controlling lateral passage of said blade as said blade drops below level of said head means with the large diameter portion of said holddown opening receiving said head means, said drive means comprising drive pin means upstanding from said platform adjacent said head means and having a top spaced above said platform to a height about equal to the thickness of said blade.

11. The apparatus of claim 7 in which said chuck has a top face up from which said golddown screw extends and above which said enlarged head means is substantially centrally located, a pair of relatively short, intermediate diameter, drive pins fixedly upstanding from said platform top face adjacent respective front corners thereof, a pair of lesser diameter, taller, guide pins fixedly upstanding from said top face of said chuck platform adjacent respective rear corners thereof, each drive pin being aligned in front of a corresponding said guide pin, said screw being substantially uniformly surrounded by said pins in radially spaced relation thereto, means limiting the extent to which said screw can be unthreaded from the top face of the platform and defining a topmost position of said head means above said platform, said drive pins having tops spaced above the top face of the platform by about the thickness of said blade, the bottom of said head means at its maximum height above the platform top face being spaced above the drive pins by an extent exceeding the thickness of the blade, said guide pins extending to a height above the platform top face between the top and bottom of said head means in its upper most position above the platform, said blade holddown opening being of key-hole shape with a forward end of diameter larger than said head means for allowing the blade to slip downward over said head means, said key hole shaped holddown opening having a rear end portion smaller in diameter than said head means but of diameter to receive laterally slidably therein said shank of said holddown screw, elongate drive openings flanking opposite sides of the smaller diameter portion of said key-hole shaped holddown opening, said drive openings being on opposite sides of said holddown opening and parallel to the longitudinal axis of the holddown opening, the drive openings having enlarged diameter front ends for receiving the drive pins and the drive openings having rear ends of lesser diameter for snugly receiving the upstanding guide pins with said head means covering the small diameter end portion of said key-hole shape blade opening, said locking means comprising means adjacent the perimeter of the small diameter end portion of said key-hole shaped holddown opening for engaging the bottom face of said head means with said pins snugly received in said drive openings for oscillating driving of said blade by said chuck through all four said pins.

12. A chuck for mounting on and oscillatory driving by a powered medical handpiece for oscillatory driving of blades, including cast cutter blades, said chuck comprising:

a platform for mounting on and oscillatory driving by a medical handpiece;

threaded clamp means for continuously maintaining threaded engagement with said platform throughout installation and removal of a blade with respect to said platform, said clamp means being captively located on and threaded with respect to said platform, said clamp means compressing a radially enlarged head means threadably adjustable toward said platform for clamping a blade fixedly to said platform and threadedly adjustable away from said platform for unclamping a blade from said platform;

keeper means capturing said clamp means for limiting spacing of said head means from said platform between a captive tight position clamping a blade to said platform and a captive loose position allowing sliding of a blade along said platform laterally out of range of clamping engagement by said head means despite continued engagement by said clamp means with said platform;

drive means fixed with respect to and upstanding from a top face of said platform at a location radially offset from said clamp means and moveable through an arc upon oscillatory driving of said chuck by a powered medical handpiece, said upstanding drive means being engageable with a blade for oscillating same in response to oscillatory driving by a medical handpiece.

13. The apparatus of claim 12 in which said clamp means comprises a screw, said head means comprising a relatively large diameter head on said screw, said screw having a relatively small diameter shank dependent from said head and an intermediate diameter threaded sub-shank dependent from said shank and threaded into a hole in said platform, said keeper means extending laterally into said hole in said platform into adjacency with said relatively small diameter shank so as to interfere with said intermediate diameter sub-shank and thereby prevent threaded escape of said screw from said hole.

* * * * *

UNITED STATES PATENT AND TRADEMARK OFFICE
CERTIFICATE OF CORRECTION

PATENT NO. : 5,702,415

DATED : December 30, 1997

INVENTOR(S) : John T. MATTHAI, et al.

It is certified that error appears in the above-indentified patent and that said Letters Patent is hereby corrected as shown below:

Column 13, line 11; change "enlarqed" to ---enlarged---.

line 14; change "qing" to ---ping---.

Column 14, line 63; change "opeing" to ---opening---.

Column 15, line 14; change "golddown" to ---holddown---.

Please add the following claim:

14. The apparatus of Claim 4 including means defining an entry path for a blade into locked engagement on said chuck, said entry path comprising respective segments directed rearward over the top of said head means, down along said head means, forward under said head means and down to said platform, and permitting a blade to be substantially parallel to the platform as it moves along said entry path.

Signed and Sealed this

Twenty-ninth Day of December, 1998

*Attest:*

BRUCE LEHMAN

*Attesting Officer*     *Commissioner of Patents and Trademarks*